(12) United States Patent
De Castro et al.

(10) Patent No.: US 11,359,068 B2
(45) Date of Patent: Jun. 14, 2022

(54) ENZYMATIC PROCESS FOR DEPOLYMERIZATION OF POST-CONSUMER POLY(ETHYLENE TEREPHTHALATE) BY A GLYCOLYSIS REACTION, PROCESS FOR RECYCLING POST-CONSUMER POLY(ETHYLENE TEREPHTHALATE), AND RECYCLED POLY(ETHYLENE TEREPHTHALATE)

(71) Applicant: PETROLEO BRASILEIRO S.A.—PETROBRAS, Rio de Janeiro (BR)

(72) Inventors: Aline Machado De Castro, Rio de Janeiro (BR); Adriano Carniel De Oliveira, Duque de Caxias (BR); Erika de Araújo Valoni, Rio de Janeiro (BR); Danielle Altomari Teixeira, Rio de Janeiro (BR); Cesar Rezende Da Motta, Rio de Janeiro (BR)

(73) Assignee: PETROLEO BRASILEIRO S.A.—PETROBRAS, Rio de Janeiro (BR)

(*) Notice: Subject to any disclaimer, the term of this patent is extended or adjusted under 35 U.S.C. 154(b) by 274 days.

(21) Appl. No.: 16/468,582

(22) PCT Filed: Sep. 14, 2017

(86) PCT No.: PCT/GB2017/052719
§ 371 (c)(1),
(2) Date: Jun. 11, 2019

(87) PCT Pub. No.: WO2019/053392
PCT Pub. Date: Mar. 21, 2019

(65) Prior Publication Data
US 2020/0255621 A1    Aug. 13, 2020

(51) Int. Cl.
C08J 11/24 (2006.01)
C08J 11/10 (2006.01)
C12N 9/18 (2006.01)

(52) U.S. Cl.
CPC .............. *C08J 11/105* (2013.01); *C08J 11/24* (2013.01); *C12N 9/18* (2013.01); *C08J 2367/02* (2013.01); *C12Y 301/01003* (2013.01); *C12Y 301/01074* (2013.01)

(58) Field of Classification Search
USPC ......................................... 528/190, 193, 194
See application file for complete search history.

(56) References Cited

FOREIGN PATENT DOCUMENTS

| | | |
|---|---|---|
| BR | PI 0605201-0 A | 8/2008 |
| JP | 2003-055300 A | 2/2003 |
| WO | 00/47659 A1 | 8/2000 |
| WO | 2013/025186 A1 | 2/2013 |
| WO | 2014/079844 A1 | 5/2014 |

OTHER PUBLICATIONS

Aline Machado De Castroa et al., "A novel process for poly(ethylene terephthalate) depolymerization via enzyme-catalyzed glycolysis", Biochemical Engineering Journal, Elsevier, Amsterdam, NL, Aug. 15, 2017, pp. 64-68, vol. 124, XP085065339.
International Search Report of PCT/GB2017/052719 dated Feb. 19, 2018 [PCT/ISA/210].
Written Opinion of PCT/GB2017/052719 dated Feb. 19, 2018 [PCT/ISA/237].

*Primary Examiner* — Terressa Boykin
(74) *Attorney, Agent, or Firm* — Sughrue Mion, PLLC

(57) ABSTRACT

The present invention relates to an enzymatic process for depolymerization of post-consumer poly(ethylene terephthalate) by a glycolysis reaction. This invention also relates to a process for recycling post-consumer poly(ethylene terephthalate) and to the recycled poly(ethylene terephthalate) obtained by said process.

8 Claims, No Drawings

ENZYMATIC PROCESS FOR DEPOLYMERIZATION OF POST-CONSUMER POLY(ETHYLENE TEREPHTHALATE) BY A GLYCOLYSIS REACTION, PROCESS FOR RECYCLING POST-CONSUMER POLY(ETHYLENE TEREPHTHALATE), AND RECYCLED POLY(ETHYLENE TEREPHTHALATE)

CROSS REFERENCE TO RELATED APPLICATIONS

This application is a National Stage of International Application No. PCT/GB2017/052719 filed Sep. 14, 2017, the contents of which are incorporated herein by reference in their entirety.

FIELD OF THE INVENTION

The present invention relates to an enzymatic process for depolymerization of post-consumer poly(ethylene terephthalate) by a glycolysis reaction, to a process for recycling post-consumer poly(ethylene terephthalate) and to the resultant recycled poly(ethylene terephthalate).

BACKGROUND OF THE INVENTION

Poly(ethylene terephthalate), better known as PET, is a type of plastic that is much used in the manufacture of containers that form part of the everyday life of the majority of the population, since containers made of PET are usually employed for packaging liquids, from medicines to beverages. In the case of beverages, especially carbonated beverages, PET bottles are usually employed owing to their reduced permeability to gases, compared to other polymers used in the manufacture of packaging. Poly(ethylene terephthalate) may also be found in other types of packaging and in other sectors of industry, such as textiles, which uses the material as raw material for the manufacture of fabrics.

From a chemical standpoint, PET is a thermoplastic polymer formed by the reaction between terephthalic acid (TPA) and ethylene glycol. One of the great advantages of PET is that it can be reprocessed several times by the same or by some other transformation process, facilitating and favouring its recycling and continuous use in the production chain.

For this reason, PET is one of the most recycled plastics worldwide. Its recycling offers numerous advantages over other packaging from the standpoint of the energy consumed, water consumption, environmental impact, and social benefits, among others.

However, although it is a recyclable product with a low cost of production, unsuitable manufacture and disposal mean that containers made of PET represent an enormous danger for the environment and for human health.

The post-consumer impacts are caused by containers sent to landfill sites and especially by those that are discarded directly in the natural environment. In the case of containers discarded correctly, we have the impacts caused by the activities of collection and transport of waste, mainly atmospheric emissions ($CO_2$). Furthermore, landfill sites are increasingly remote from large conurbations and there is a chronic problem of lack of space for disposal of the waste produced. The cost of collection and disposal of waste is constantly increasing. Accordingly, various resources that could be invested in health, education, and security end up subsidizing this increased expenditure associated with waste that is constantly being generated.

In the case when containers made of PET are not disposed of correctly and are discarded directly in the natural environment, there is an even more serious problem. Generally rivers are the final destination of containers made of PET, increasing water pollution and the problem of floods. The plastic takes more than 100 years to decompose and may even cause loss of biodiversity. Fragments of plastic may be consumed by animals, causing their death. The impact of incorrect disposal can even be seen in the oceans, where studies indicate that most bodies of water are already contaminated.

Thus, various studies are now being conducted into recycling processes for reuse of the material of post-consumer PET containers for synthesis of new polymer. This reuse may represent large economic advantages for the companies that manufacture this polymer, further reducing dependence on new raw materials of fossil origin.

The document WO 2014/079844, for example, describes a process for degradation of ground PET bottles by a hydrolysis reaction, employing a cutinase from *Thermobifida cellulosilytica* DSM44535 as biocatalyst.

The article by Kim and Song (*Fibers and Polymers*, 2006, vol. 7, p. 339-343) assesses various commercial lipases for the treatment of PET-based textiles, by a hydrolysis process.

Moreover, the article by Muller et al. (*Macromolecules*, 2009, vol. 42, p. 5128-5138) investigates various commercial lipases in processes of hydrolysis of samples of PET from bottles and in the form of pellets.

However, the documents cited above perform depolymerization of PET by a hydrolysis reaction, in which the main product is typically terephthalic acid (TPA) which, when returned to the polymerization process, must then be esterified with ethylene glycol (esterification reactions) to obtain bis-hydroxyethylene terephthalate (BHET) in the next step, and then carry out the polymerization process for synthesis of new PET.

As another drawback, when hydrolysis processes are adopted, the products from depolymerization must be recovered from the liquid phase for the subsequent process of repolymerization, since the presence of water is undesirable in the esterification reactions.

With the aim of overcoming these problems, studies were conducted in an attempt to obtain optimized processes of the reaction of depolymerization of PET containers.

In this connection, the Brazilian patent document PI 0605201-0 teaches a method for obtaining PET oligomers, such as bis-hydroxyethylene terephthalate (BHET) and bis-hydroxypropylene terephthalate (BHPT), on the basis of a chemical process by means of the glycolysis reaction of PET, employing zinc acetate as catalyst. Carrying out a glycolysis reaction has advantages, in that the BHET obtained can be used in the repolymerization process for synthesis of new PET in a subsequent step of the process.

Another advantage is that in the glycolysis reactions, ethylene glycol is the liquid phase, which can be used directly in the repolymerization process.

Similarly, document WO 00/47659 discloses a process for depolymerizing and purifying contaminated post-consumer polyester by a glycolysis reaction. This document describes, as suitable catalysts, known transesterification catalysts, such as salts of manganese, zinc, antimony, titanium, tin or germanium, which increase the rate of glycolysis.

However, the chemical process employing metal or alkaline catalysts described above has disadvantages, because besides causing environmental impacts, said catalysts remain in the mixture of products obtained, and may interfere with the repolymerization process.

Thus, there is still a need to provide an optimized process for depolymerization of post-consumer PET that is safer, more economical and has less environmental impact.

As will be described in greater detail below, the present invention provides a practical and efficient solution to the problems of the prior art described above.

SUMMARY OF THE INVENTION

The present invention relates to an enzymatic process for depolymerization of post-consumer poly(ethylene terephthalate) by a glycolysis reaction. This invention also relates to a process for recycling post-consumer poly(ethylene terephthalate) and to the recycled poly(ethylene terephthalate) obtained by said process. The invention is defined in the claims.

According to a first aspect of the disclosure, there is a provided an enzymatic process for depolymerization of post-consumer poly(ethylene terephthalate) by a glycolysis reaction, comprising steps of:

a) adding poly(ethylene terephthalate) and ethylene glycol to a stirred tank reactor;

b) adjusting the temperature to a value between 20 and 100° C. and stirring at a speed between 20 and 300 rpm; and c) adding a charge of a catalyst between 0.01 to 1.0 g/gPET to the reactor, wherein the catalyst comprises one or more enzymes of the cutinase, esterase or lipase type, wherein, after a period of time of from 2 to 30 days, a final stream comprising terephthalic acid (TPA), mono-hydroxyethylene terephthalate (MHET) and bis-hydroxyethylene terephthalate (BHET) is obtained, which comprises 30 to 95 mol % of BHET based on the total of final products of the reaction.

According to a further aspect of the disclosure, there is a provided a process for recycling post-consumer poly(ethylene terephthalate), comprising a step of using the final stream comprising 30 to 95 mol % of bis-hydroxyethylene terephthalate (BHET) obtained in step c) of the enzymatic process for depolymerization of PET.

According to a yet further aspect of the disclosure, there is provided recycled poly(ethylene terephthalate), characterized in that it is obtained by the process of the invention.

DETAILED DESCRIPTION OF THE INVENTION

The present disclosure relates to an enzymatic process for depolymerization of post-consumer poly(ethylene terephthalate) by a glycolysis reaction, in which the product stream obtained at the end of the process is enriched with bis-hydroxyethylene terephthalate (BHET), which can be reused in a process of repolymerization of new PET.

This reuse offers surprising advantages since the main product obtained in reactions of depolymerization of PET is typically terephthalic acid which, on being returned to the polymerization process, must then be esterified with ethylene glycol (esterification reactions), to reach BHET in a subsequent step.

In contrast, in the depolymerization process of the present disclosure, the final product stream obtained is already enriched with bis-hydroxyethylene terephthalate (BHET), which can be reused in a subsequent step of the process for recycling post-consumer PET for the synthesis of new PET, thus reducing energy expenditure, as well as dependence on p-xylene from third parties, which is used as a raw material for the synthesis of terephthalic acid.

The enzymatic process for depolymerization of PET now proposed is carried out in a stirred tank reactor, and is preferably a batch process that is carried out in a reactor of the CSTR (continuous flow stirred-tank reactor) type, and optionally employs an initial pre-treatment step.

If there is no pre-treatment, the reaction is carried out using raw poly(ethylene terephthalate), whereas when the optional pre-treatment step is employed, the process is carried out using fragments of poly(ethylene terephthalate), which undergo washing or soaking. In the case of washing, the PET fragments are preferably washed with aqueous solution containing a non-ionic surfactant, for example Tween-80, followed by washing with water. In the case of soaking, the PET fragments are preferably exposed to the solvent ethylene glycol, or mixtures thereof with other alcohols, for short periods from 10 to 30 min at high temperatures varying between 100 and 130° C., or for longer periods of 12 to 24 hours at milder temperatures varying between 20 and 80° C.

For the reaction of depolymerization of poly(ethylene terephthalate) by a glycolysis reaction, raw poly(ethylene terephthalate) or the pre-treated PET fragments are first added to the reactor, with ethylene glycol as solvent. Then the temperature is adjusted and stabilized to the desired value, preferably from 20 to 100° C., and more preferably from 30 to 90° C., preferably at atmospheric pressure and with stirring at speeds preferably in the range from 20 to 300 rpm. After setting these parameters, a charge of catalyst comprising one or more enzymes is added to the reactor and the glycolysis reaction begins.

Suitable enzymatic catalysts include commercially available cutinases and lipases, preferably Novozym 51032®, from the company Novozymes, which corresponds to a cutinase from *Humicola insolens* expressed in *Aspergillus*, and Lipozyme CALB®, lipase B from *Candida antarctica*. The catalyst charge employed can vary depending on the type of enzyme(s) used and is preferably about 0.01 to 1.0 g/gPET, more preferably about 0.01 to 0.5 g/gPET.

After a period of approximately 2 to 30 days, preferably from 7 to 28 days, a final product stream comprising terephthalic acid (TPA), mono-hydroxyethylene terephthalate (MHET) and bis-hydroxyethylene terephthalate (BHET) is obtained, which is enriched with bis-hydroxyethylene terephthalate (BHET). "BHET-enriched" final product stream means a final product stream comprising BHET in concentrations that vary from 2 to 85 µmol/L, which represents a percentage of about 30 to 95 mol % of BHET based on the total of the final products of the reaction. A percentage esterification above 70% may be achieved at the end of said process.

The present disclosure also relates to a process for recycling post-consumer poly(ethylene terephthalate) by a glycolysis reaction that comprises, besides the steps described here for the enzymatic process for depolymerization of post-consumer poly(ethylene terephthalate), the additional step of utilizing the final product stream obtained in said process of depolymerization of poly(ethylene terephthalate) in a more advanced step in the process for polymerization of recycled PET (repolymerization). This reuse not only provides energy savings, but also economic, environmental, health and security benefits.

The present disclosure further relates to said recycled poly(ethylene terephthalate), obtained by the process described and claimed here.

The following examples illustrate the various embodiments of the present invention.

Examples

1. Glycolysis of Raw PET from Bottles

With stirring at 150 rpm at 37° C., the enzyme Novozym51032® (NZ) or the enzyme lipase B from *Candida antarctica* (CALB) was brought into contact with fragments of PET from chopped bottles, with ethylene glycol as solvent. A catalyst charge of 0.1 g/gPET was added, and after 7 and 14 days, concentrations of BHET of 2.75 and 7.08 μmol/L, respectively, were obtained. The molar fractions of the main products (TPA, BHET and MHET) for two charges of catalyst and enzymes are presented in Table 1, and compared with the results of a hydrolysis reaction, carried out in the same conditions. It can be seen that carrying out the glycolysis reaction especially with the enzyme NZ led to enrichment of the final solution with BHET, so that this became the main product of the reaction, with the charge of 0.1 g/gPET. It can also be seen from the table that carrying out the glycolysis step, as opposed to hydrolysis, reduced the molar fractions of the compound MHET, which is an intermediate in depolymerization, between BHET and TPA.

TABLE 1

Molar fractions of the main products of the glycolysis and hydrolysis reactions.

| Enzyme and charge (g/g) | Time (days) | Glycolysis TPA | BHET | MHET | Hydrolysis TPA | BHET | MHET |
|---|---|---|---|---|---|---|---|
| NZ-0.1 | 7 | 0.677 | 0.323 | 0.000 | 0.475 | 0.053 | 0.472 |
|  | 14 | 0.386 | 0.614 | 0.000 | 0.454 | 0.161 | 0.384 |
| NZ-0.5 | 7 | 0.649 | 0.140 | 0.212 | 0.539 | 0.031 | 0.429 |
|  | 14 | 0.312 | 0.417 | 0.271 | 0.620 | 0.032 | 0.348 |
| CALB-0.1 | 7 | 0.631 | 0.369 | 0.000 | 0.752 | 0.214 | 0.035 |
|  | 14 | 0.394 | 0.315 | 0.290 | 0.661 | 0.306 | 0.033 |
| CALB-0.5 | 7 | 0.409 | 0.248 | 0.343 | 0.613 | 0.202 | 0.185 |
|  | 14 | 0.293 | 0.311 | 0.396 | 0.575 | 0.249 | 0.176 |

2. Glycolysis of Pre-Treated Bottle PET A

Fragments of PET from bottles underwent the following pre-treatment:

A. Washing with aqueous solution containing 2% of Tween-80 for 1 h at 50° C., followed by washing with water for 1 h and drying for 24 h.

With stirring at 150 rpm at 37° C., the enzyme Novozym51032® (NZ) or the enzyme lipase B from *Candida antarctica* (CALB) was brought into contact with fragments of PET from chopped bottles and pre-treated, with ethylene glycol as solvent and a catalyst charge of 0.1 g/gPET. When pre-treated PET A was used, after 14 days, a concentration of BHET of 24.71 μmol/L was obtained, and after 28 days, percentage esterification of the mixture of 87.8% was obtained, with the enzyme NZ. The molar fractions of the main products (TPA, BHET and MHET) for two charges of catalyst and enzymes are presented in Table 2. Note that in this case BHET corresponded to 83.3% of the main products of the reaction, when pre-treated PET A was brought into contact with the enzyme NZ.

TABLE 2

Molar fractions and concentrations of the main products of the glycolysis reactions with pre-treated PET A.

| Enzyme | Time (days) | Concentrations (μmo/L) TPA | BHET | MHET | Molar fractions TPA | BHET | MHET |
|---|---|---|---|---|---|---|---|
| NZ | 7 | 18.66 | 14.95 | 0.45 | 0.548 | 0.439 | 0.013 |
|  | 14 | 6.65 | 24.71 | 0.79 | 0.207 | 0.769 | 0.025 |
|  | 21 | 2.58 | 18.57 | 1.93 | 0.112 | 0.805 | 0.084 |
|  | 22 | 3.14 | 17.91 | 1.44 | 0.140 | 0.796 | 0.064 |
|  | 28 | 1.65 | 17.61 | 1.88 | 0.078 | 0.833 | 0.089 |
| CALB | 7 | 9.99 | 7.87 | 1.02 | 0.529 | 0.417 | 0.054 |
|  | 14 | 3.71 | 9.45 | 0.00 | 0.282 | 0.718 | 0.000 |
|  | 21 | 4.32 | 5.92 | 1.14 | 0.380 | 0.520 | 0.100 |
|  | 22 | 2.07 | 6.29 | 1.23 | 0.216 | 0.656 | 0.128 |
|  | 28 | 1.46 | 5.59 | 1.48 | 0.171 | 0.656 | 0.174 |

3. Glycolysis of Pre-Treated Bottle PET B

Fragments of PET from bottles underwent the following pre-treatment:

B: Soaking in ethylene glycol (proportion 1 g PET to 25 mL ethylene glycol) for 22 h at 37° C.

With stirring at 150 rpm at 37° C., the enzyme Novozym51032® (NZ) or the enzyme lipase B from *Candida antarctica* (CALB) was brought into contact with fragments of PET from chopped bottles and pre-treated, with ethylene glycol as solvent and a catalyst charge of 0.1 g/gPET. When pre-treated PET B was used, after 14 days, a concentration of BHET of 84.42 μmol/L was obtained with the enzyme CALB and after 22 days, percentage esterification of 87.6% was obtained with the enzyme NZ. The molar fractions of the main products (TPA, BHET and MHET) for the two charges of enzymes are presented in Table 3. Note that in this case BHET corresponded to 81.3% of the main products of the reaction, when pre-treated PET B was brought into contact with the enzyme NZ.

TABLE 3

Molar fractions and concentrations of the main products of the glycolysis reactions with pre-treated PET B.

| Enzyme | Time (days) | Concentrations (μmol/L) | | | Molar fractions | | |
|---|---|---|---|---|---|---|---|
| | | TPA | BHET | MHET | TPA | BHET | MHET |
| NZ | 7 | 12.28 | 8.65 | 0.64 | 0.569 | 0.401 | 0.030 |
| | 14 | 6.50 | 10.97 | 0.00 | 0.372 | 0.628 | 0.000 |
| | 21 | 2.76 | 6.60 | 1.12 | 0.263 | 0.630 | 0.107 |
| | 22 | 0.52 | 6.84 | 1.05 | 0.062 | 0.813 | 0.124 |
| | 28 | 1.99 | 6.52 | 1.83 | 0.192 | 0.631 | 0.177 |
| CALB | 7 | 15.89 | 31.47 | 2.15 | 0.321 | 0.636 | 0.043 |
| | 14 | 124.22 | 84.42 | 8.58 | 0.572 | 0.389 | 0.040 |
| | 21 | 4.21 | 56.80 | 17.62 | 0.054 | 0.722 | 0.224 |
| | 22 | 4.33 | 60.53 | 20.66 | 0.051 | 0.708 | 0.242 |
| | 28 | 3.88 | 74.03 | 32.99 | 0.035 | 0.668 | 0.297 |

4. Glycolysis of Pre-Treated Bottle PET C

Fragments of PET from bottles underwent the following pre-treatment:

C: Soaking in ethylene glycol mixture (proportion 1 g PET to 25 mL ethylene glycol) for 22 h at 70° C.

With stirring at 150 rpm at 37° C., the enzyme Novozym51032® (NZ) or lipase B from *Candida antarctica* (CALB) was brought into contact with fragments of PET from chopped bottles and pre-treated, with ethylene glycol as solvent and charge of catalyst NZ of 0.1 g/gpET. When pre-treated PET C was used, after 14 days a concentration of BHET of 15.51 μmol/L was obtained, and percentage esterification of the mixture of 84.3%, with the enzyme NZ. The concentrations and molar fractions of the main products (TPA, BHET and MHET) for the two enzymes are presented in Table 4. Note that in this case BHET corresponded to 80.3% of the main products of the reaction, when pre-treated PET C was brought into contact with the enzyme NZ.

TABLE 4

Molar fractions and concentrations of the main products of the glycolysis reactions with pre-treated PET C.

| Enzyme | Time (days) | Concentrations (μmol/L) | | | Molar fractions | | |
|---|---|---|---|---|---|---|---|
| | | TPA | BHET | MHET | TPA | BHET | MHET |
| NZ | 7 | 1.04 | 4.78 | 0.47 | 0.164 | 0.762 | 0.074 |
| | 14 | 1.41 | 9.79 | 0.99 | 0.116 | 0.803 | 0.081 |
| | 21 | 20.81 | 15.51 | 2.14 | 0.395 | 0.531 | 0.075 |
| CALB | 7 | 1.31 | 2.53 | 1.38 | 0.255 | 0.479 | 0.266 |
| | 14 | 1.06 | 3.67 | 1.45 | 0.177 | 0.593 | 0.229 |
| | 21 | 1.07 | 4.56 | 1.82 | 0.143 | 0.612 | 0.245 |

5. Glycolysis of Pre-Treated Bottle PET D

Fragments of PET from bottles underwent the following pre-treatment:

D: Soaking in ethylene glycol solution (proportion 1 g PET to 25 mL ethylene glycol) for 20 min at 121° C.

With stirring at 150 rpm at 37° C., the enzyme Novozym51032® (NZ) or lipase B from *Candida antarctica* (CALB) was brought into contact with fragments of PET from chopped bottles and pre-treated, with ethylene glycol as solvent and charge of catalyst NZ of 0.1 g/gpET. When pre-treated PET D was used, after 14 days a concentration of BHET of 35.08 μmol/L was obtained, and after 21 days, percentage esterification of the mixture of 85.1%, with the enzyme NZ. The molar fractions of the main products (TPA, BHET and MHET) for the two enzymes are presented in Table 5. Note that in this case BHET corresponded to 75.4% of the main products of the reaction, when pre-treated PET D was brought into contact with the enzyme NZ.

TABLE 5

Molar fractions and concentrations of the main products of the glycolysis reactions with pre-treated PET D.

| Enzyme | Time (days) | Concentrations (μmol/L) | | | Molar fractions | | |
|---|---|---|---|---|---|---|---|
| | | TPA | BHET | MHET | TPA | BHET | MHET |
| NZ | 7 | 2.85 | 22.34 | 4.35 | 0.097 | 0.756 | 0.147 |
| | 14 | 1.84 | 23.74 | 5.96 | 0.059 | 0.754 | 0.188 |
| | 21 | 1.58 | 35.08 | 11.06 | 0.034 | 0.742 | 0.224 |
| CALB | 7 | 1.17 | 15.86 | 6.48 | 0.050 | 0.675 | 0.275 |
| | 14 | 1.26 | 12.63 | 5.80 | 0.067 | 0.690 | 0.243 |
| | 21 | 1.60 | 12.65 | 12.50 | 0.060 | 0.473 | 0.467 |

As may be deduced from the above examples, the enzymatic process for depolymerization of post-consumer PET by a glycolysis reaction is extremely advantageous, since the product stream obtained at the end is enriched with BHET, which can be reused in the process of repolymerization for synthesis of new PET in a subsequent step of the process, thus reducing the energy expenditure and making it more economically viable.

Furthermore, there is less dependence on raw materials from third parties, for example p-xylene, which is necessary for the synthesis of terephthalic acid, which is the raw material in the process for synthesis of the polyester poly (ethylene terephthalate). From the environment and health standpoint, the enzymatic process for the depolymerization of PET is safer, since the biocatalyst (enzymes) employed is renewable, non-corrosive and biodegradable, and it is carried out at milder temperatures and can be carried out at atmospheric pressure. This guarantees additional operational safety of the unit that will employ it on a large scale.

Numerous variations falling within the scope of protection of the present application are permitted. The present invention is not limited to the configurations/particular embodiments described above.

The invention claimed is:

1. Enzymatic process for depolymerization of post-consumer poly(ethylene terephthalate) by a glycolysis reaction, comprising steps of:
   a) adding poly(ethylene terephthalate) and ethylene glycol to a stirred tank reactor;
   b) adjusting the temperature to a value between 20 and 100° C. and stirring at a speed between 20 and 300 rpm; and
   c) adding a charge of a catalyst between 0.01 to 1.0 g/gPET to the reactor, wherein the catalyst comprises one or more enzymes of the cutinase, esterase or lipase type,
   wherein, after a period of time of from 2 to 30 days, a final stream comprising terephthalic acid (TPA), mono-hydroxyethylene terephthalate (MHET) and bis-hydroxyethylene terephthalate (BHET) is obtained, which comprises 30 to 95 mol % of BHET based on the total of final products of the reaction.

2. Process according to claim 1, wherein the process is carried out in batch mode in a reactor of the CSTR type.

3. Process according to claim 1, additionally comprising a pre-treatment step before step a).

4. Process according to claim 3, wherein the pre-treatment step comprises washing with non-ionic surfactant or soaking with ethylene glycol, or mixtures thereof with other alcohols.

5. Process for according to claim 1, wherein the temperature in step b) is between 30 and 90° C.

6. Process according to claim 1, wherein the one or more enzymes of the cutinase, esterase and lipase type are selected from a cutinase from *Humicola insolens* expressed in *Aspergillus*; and CALB, lipase B from *Candida antarctica*.

7. Process for recycling post-consumer poly(ethylene terephthalate), comprising a step of
   using the final stream comprising 30 to 95 mol % of bis-hydroxyethylene terephthalate (BHET) obtained in step c) of the enzymatic process for depolymerization of PET, as defined in claim 1, in the repolymerization of a recycled poly(ethylene terephthalate).

8. Recycled poly(ethylene terephthalate), characterized in that it is obtained by the process as defined in claim 7.

* * * * *